United States Patent
Byrd et al.

(10) Patent No.: US 8,349,223 B1
(45) Date of Patent: Jan. 8, 2013

(54) BORONATED POLYPHOSPHINOHYDRAZIDE FIRE RETARDANT

(75) Inventors: Norman R. Byrd, Villa Park, CA (US); Douglas G. Soden, San Pedro, CA (US); Arthur Rojo, Cypress, CA (US)

(73) Assignee: The Boeing Company, Chicago, IL (US)

(*) Notice: Subject to any disclaimer, the term of this patent is extended or adjusted under 35 U.S.C. 154(b) by 639 days.

(21) Appl. No.: 12/563,617

(22) Filed: Sep. 21, 2009

(51) Int. Cl.
*C09K 21/00* (2006.01)
*C09K 21/10* (2006.01)
*C09K 21/12* (2006.01)
*C07F 9/02* (2006.01)
*C07F 5/02* (2006.01)
*C01B 35/10* (2006.01)
*C07C 241/04* (2006.01)
*C07C 243/10* (2006.01)

(52) U.S. Cl. ........ 252/609; 252/601; 423/277; 423/284; 564/14; 564/464; 568/2

(58) Field of Classification Search .................. 252/609; 564/14, 464; 568/2; 423/277, 284
See application file for complete search history.

(56) References Cited

U.S. PATENT DOCUMENTS

| | | | |
|---|---|---|---|
| 3,107,231 A * | 10/1963 | Malz et al. | 524/137 |
| 3,228,814 A * | 1/1966 | Jenkins et al. | 149/22 |
| 4,092,108 A * | 5/1978 | Valko et al. | 8/194 |
| 4,308,197 A | 12/1981 | Byrd et al. | |
| 4,364,994 A | 12/1982 | Fogelberg | |
| 4,403,075 A | 9/1983 | Byrd et al. | |
| 4,582,932 A | 4/1986 | Byrd et al. | |
| 4,588,838 A | 5/1986 | Byrd | |
| 4,739,115 A | 4/1988 | Byrd et al. | |
| 5,516,940 A * | 5/1996 | Katti et al. | 564/14 |

* cited by examiner

*Primary Examiner* — Peter F Godenschwager
(74) *Attorney, Agent, or Firm* — Alston & Bird LLP (57) ABSTRACT

Boronated polyphosphinohydrazide fire retardants are provided having the basic structural unit:

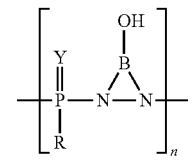

wherein,

Y is O or S;

R can be selected from H, alkyl (e.g., linear, branched, saturated, or unsaturated), aryl, heterocyclic, cycloaliphatic (e.g., saturated or unsaturated), or a metallocene (e.g., ferrocene, zirconocene or the like); and n can be selected from 1 to 500.

16 Claims, 4 Drawing Sheets

BORONATED POLYPHOSPHINOHYDRAZIDE FIRE RETARDANT

Embodiments of the present invention are related to boronated polyphosphinohydrazide fire retardants.

BACKGROUND

Graphite design, fabrication, test and analytical studies have shown that the use of high-stiffness, high-strength composites such as graphite/resin composites can reduce the weight of structural components by as much as 50%, improve structure efficiency, and provide significant benefits in cost and performance.

Accordingly, considerable interest has arisen in the use of graphite composites in both internal and external aircraft applications as well as in engine nacelles. For instance, in external applications such as in fairings, skins, rudders, stabilizers, flaps and doors, as well as in engine nacelles, it would be desirable for the resin to resist burning and also prevent short lengths of the graphite fiber from spreading to other areas. For internal applications such as cargo compartment liners and passenger compartment floor panels, it would be desirable to utilize a resin that eliminates or mitigates the level of flammability, smoke, and toxicity.

Further, in the nacelle, fire spreading from the hot zone through an acoustic panel fire wall could affect fuel lines, electrical equipment and hydraulic fluids, among other items. For this reason, the FAA has established a fire-safe requirement that any fire wall in an aircraft should be capable of withstanding a 2000° F. flame for 15 minutes.

Any organic material will burn if its ignition temperature is reached. However, extensive research has been conducted for a number of years to reduce the hazards from fire. In most cases, fire-retardant additives have been chosen. In other instances, polymer structures have been modified in order to reduce burning tendencies. Thus, the flammability of polymeric systems can be controlled by introducing elements which interfere with gas-phase oxidation reactions in the flame zone or modify the pyrolysis and decomposition reaction in the solid phase. Both bromine and chlorine are used extensively in the formulation of flame-retardant chemicals for polymers and operate by interfering with vapor phase combustion reactions. Organophosphorous compounds interfere with the combustion reaction in the condensed phase.

There are two general approaches to imparting flame retardance to materials, reactive and additive. Reactive fire-retardant chemicals enter into chemical reaction and become an integral part of the polymer structure; whereas the additive chemical is physically dispersed in the polymer but does not become part of the polymer structure. Generally, those compounds containing a halogen (usually chlorine or bromine), phosphorous, or nitrogen have been found to be effective flame retardants. Reactive flame-retardant intermediates are normally used in the manufacture of unsaturated polyesters, alkyds, epoxies and polyurethanes. However, the term "flame retardant" becomes moot. For instance, materials that are flame retardants at relatively low heat flux (e.g., a burning match) can have little or no effect in the high heat flux that accompanies a fuel spill or some other fire generating a 2000° F. flame.

Although a large class of brominated fire retardants has been used quite extensively, the toxic byproducts generated have resulted in their use being phased out. Hence, as a replacement of the brominated compounds, the phosphorylated compounds have been used increasingly. One class of phosphorylated compounds has been polyphosphinohydrazides generalized by the structure represented by Formula 1:

(1)

where R is H, alkyl (e.g., linear, branched, saturated, or unsaturated), aryl, heterocyclic, cycloaliphatic (e.g., saturated or unsaturated), or a metallocene (e.g., ferrocene, zirconocene or the like).

Although polyphosphinohydrazides according to Formula 1 have performed well and have been able to replace the brominated fire retardants, they have not done well above 2000° F. As such there remains a need for a fire retardant that exhibits a fire retarding capability above 2000° F. There also remains a need for a fire retardant that does not generate toxic products or leach out of the resin systems. Furthermore, there remains a need for a fire retardant that exhibits a fire retarding capability above 2000° F. that leaves a structurally stable char.

BRIEF SUMMARY

Embodiments of the present invention satisfy at least some of the aforementioned needs by providing a boronated polyphosphinohydrazide fire retardant exhibiting a thermal stability at temperatures up to an including about 3000° F. The fire retardants according to embodiments of the present invention are capable of being chemically bound to a large variety of resins, adhesives, or coatings. Beneficially, fire retardants according to embodiments of the present invention can chemically bond with a base polymer structure (e.g., the fire retardant can be incorporated into the base polymer structure), which eliminates or mitigates any leaching out over time. As such, embodiments of the present invention can be uniformly available fire retardants. Another beneficial characteristic of embodiments of the present invention is their capability of forming a non-volatile stable char with structural integrity.

Embodiments of the present invention include a boronated polyphosphinohydrazide having the basic structural unit according to formula (2):

(2)

where Y can be selected from O or S; R can be selected from H, alkyl (e.g., linear, branched, saturated, or unsaturated), aryl, heterocyclic, cycloaliphatic (e.g., saturated or unsaturated), or a metallocene (e.g., ferrocene, zirconocene or the like); and n can be selected from 1 to 500.

In one aspect, at least some of the aforementioned needs are achieved, according to embodiments of the present invention, by incorporating into a resin such as a polyimide, epoxy, an acrylic, a polyamide, a polyvinyl or a polyaryl a boronated polyphosphinohydrazide. Such a mixture or composition can then by applied to a suitable substrate, such as glass cloth or carbon (graphite) cloth, to form a "prepreg," and the resin is cured to obtain a fire resistant composite or laminate.

Certain embodiments of the present invention provide a polymer resin matrix including a boronated polyphosphinohydrazide polymer mixed with a desirable base polymer. In certain embodiments according to the present invention, the polymer resin includes a mixture of a boronated polyphosphinohydrazide having the basic structural unit:

(2)

where Y can be selected from O or S; R can be H, alkyl (e.g., linear, branched, saturated, or unsaturated), aryl, heterocyclic, cycloaliphatic (e.g., saturated or unsaturated), or a metallocene (e.g., ferrocene, zirconocene or the like), and n can be selected from 1 to 500 and a polyimide, an epoxy, a polyamide, a polyvinyl, or a polyaryl resin. These polymer resins can be cured to form fire resistant composites for use in a wide variety of structural or non-structural components having the boronated polyphosphinohydrazide polymer chemically incorporated therein.

In another aspect, embodiments of the present invention provide a method for boronating a polyphosphinohydrazide. In certain embodiments, a phosphinohydrazide polymer and boric acid are reacted by preferably adding boric acid to a neat polyphosphinohydrazide polymer and agitating the mixture. Preferably, the resulting mixture is heated to about 170° F. to 210° F.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION

The present invention now will be described more fully hereinafter with reference to the accompanying drawings, in which some, but not all embodiments of the inventions are shown. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

Embodiments of the present invention provide fire resistant boronated polyphosphinohydrazide polymers that exhibit enhanced fire-retarding capabilities. That is, the addition of boron to a phosphorous/nitrogen fire retardant increases the fire retarding capability by as much as 500° F. to 1000° F. above the 2000° F. limit presently available; as well as creating a higher thermal barrier. In addition to the enhanced fire retarding capability, the boronated polyphosphinohydrazide polymers constitute fire retardants that have a high flame-initiating temperature and form stable chars with little smoke evolution. In such embodiments, the boronated polyphosphinohydrazides have following basic structural unit:

(2)

wherein, Y is O or S; R can be H, alkyl (e.g., linear, branched, saturated, or unsaturated), aryl, heterocyclic, cycloaliphatic (e.g., saturated or unsaturated), or a metallocene (e.g., ferrocene, zirconocene or the like); and n can be selected from 1 to 500. In certain embodiments of the present invention, n can range from 200 to 500, 300 to 500, or from 400 to 500. In other embodiments according to the present invention, n can range from 1 to 300, 1 to 200, or from 1 to 100.

Embodiments In certain embodiments, the boronated polyphosphinohydrazides according to Formula (2) can include a variety of independently selected moieties. In such embodiments, Y is O or S; R is H, alkyl, with straight chain or branched chain, and generally containing from about 1 to about 6 carbon atoms, e.g., methyl, ethyl, propyl, isopropyl, butyl, isobutyl, pentyl, hexyl, and isohexyl (unsaturated such as vinyl, allyl, acrylic, and acetylenic); cycloalkyl, generally containing from about 5 to about 7 carbon atoms, such as, for example, cyclopentyl, cyclohexyl, methylcyclohexyl (and unsaturated); aryl, generally containing from about 6 to about 14 carbon atoms, such as phenyl, xylyl, tolyl, naphthyl, anthracenyl, carbazole, methylnaphthyl and ethylnaphthyl; heterocyclic containing 5 to 6 members in the heterocyclic nucleus, and O, N or S as hetero atoms, e.g., furanyl, pyridyl, pyrrolyl, quinolyl and thiophene; amino, alkylamino containing from about 1 to about 8 carbon atoms in the alkyl group, e.g., methylamino, ethylamino, dimethylamino, diethylamino, arylamino containing from about 6 to about 14 carbon atoms such as phenylamino and naphthylamino, oxyalkyl containing from 1 to about 4 carbon atoms such as oxymethyl, oxyethyl, oxypropyl, and oxyaryl containing about 6 to about 14 carbon atoms such as oxyphenyl, oxytolyl and oxynaphthyl, and the like.

Boronated polyphosphinohydrazide polymers according to embodiments of the present invention are capable of being chemically bound to almost any resin and will not leach out over time. That is, the boronated polyphosphinohydrazide polymers can beneficially be chemically bonded with a base polymer used for manufacturing a myriad of structural and non-structural composites or laminates. Contrary to embodiments of the present invention, previously employed materials (e.g., brominated fire retardants) do not form a bond to the matrix resin or adhesive or coating chemical. Also, they generate toxic products. An additional benefit realized by the boronated polyphosphinohydrazide polymers according to such embodiments is their ability to form a non-volatile stable char with structural integrity. Such a benefit is not obtainable with a variety of other fire retardants. As one example, intumescent agents are dispersed particulates that do not leave structurally stable chars.

As previously referenced, the boronated polyphosphinohydrazides according to embodiments of the invention exhibit an increased thermal stability. According to certain embodiments, the boronated polyphosphinohydrazides have or exhibit thermal stability up to and including about 2200° F., 2300° F., 2400° F., 2500° F., 2600° F., 2700° F., 2800° F., 2900° F., or 3000° F.

In one aspect, embodiments of the present invention provide a polymer resin including the mixture of a boronated polyphosphinohydrazide polymer and a desirable base polymer. In one embodiment, the polymer resin can be a mixture, preferably a homogeneous solution, including a boronated polyphosphinohydrazide having the basic structural unit:

(2)

wherein,
Y is O or S; R can be selected from H, alkyl (e.g., linear, branched, saturated, or unsaturated), aryl, heterocyclic, cycloaliphatic (e.g., saturated or unsaturated), or a metallocene (e.g., ferrocene, zirconocene or the like); n can range from 1 to 500; and a polyimide, epoxy, acrylic, polyvinyl, polyamide, polyaryl, phenolic, or silicone resin.

According to certain embodiments of the present invention, a polymer resin includes the mixture of a boronated polyphosphinohydrazide polymer according to Formula (2) and a base polymer selected from a polyimide, epoxy, acrylic, polyvinyl, phenolic/Novolak, polybenzimidazole, polyquinoxaline, polypyrrole, polyaniline, polyamide, polyaryl, polyamic acid, silicone resin or combinations thereof. Embodiments including silicone preferably utilize a silicone having a vinyl side-chain or an Si atom with a hydrogen as a side group attached to the silicon atom. Embodiments including an epoxy resin preferably utilize an epoxy selected from a glycidyl amine, MY720, glycidyl ester, glycidyl bisphenol A, and epoxies including an anhydride hardener or an amine hardener. Preferred polyimides include Monsanto 703, Peti 5, Peti 298, Peti 330, and PMR-15.

According to embodiments of the present invention, polymer resin includes the mixture of a boronated polyphosphinohydrazide polymer according to Formula (2) and a base polymer, in which the boronated polyphosphinohydrazide polymer is present from 1 to 50% by weight of the polymer resin. In certain embodiments, the boronated polyphosphinohydrazide polymer is present from 3-30%, 3-20%, 5-20%, or 5-10% by weight of the polymer resin. In other embodiments, the boronated polyphosphinohydrazide polymer is present from 1-20%, 1-10%, or 1-5% by weight of the polymer resin.

In one preferred embodiment, the polymer resin includes a boronated polyphosphinohydrazide polymer selected from the group consisting of:

wherein, Y is O or S; n can be selected from 1 to 500. In this embodiment, the base polymer mixed with the boronated polyphosphinohydrazide polymer is a polyimide resin. Preferably, the polyimide resin is selected from Peti 5, Peti 298, Peti 330, Monsanto 703, PMR-15, or combinations thereof.

In another preferred embodiment, the boronated polyphosphinohydrazide is selected from the group consisting of:

Where Y is O or S; n can be selected from 1 to 500. In such embodiments, the base polymer is an epoxy-based resin.

In another aspect, embodiments of the present invention provide highly fire resistant composites or laminates particularly applicable as structural components in aircraft, e.g. in the engine nacelle, as part of the acoustic panel-fire wall structure, and capable of withstanding a flame temperature up to and including 3,000° F. The fire resistant composites and laminates include a boronated polyphosphinohydrazide polymer chemically bonded or incorporated within a base resin (e.g., a polyimide or an epoxy resin). The resulting resin (i.e., mixture of the boronated polyphosphinohydrazide polymer and the base polymer) can then be applied to or impregnated into a substrate such as glass fiber cloth or graphite fiber, to form a composite structure which is then cured. The resulting cured composite when subjected to high temperatures of the order of, about 2,000° F. to about 3,000° F. flame temperature, forms a resin char of reduced thermal conductivity which holds the fibers of the laminate together and maintains the structural stability and integrity of the composite or laminate.

In one embodiment according to the present invention, a fire resistant composite or laminate comprise a cured mixture of a boronated polyphosphinohydrazide polymer having the basic structural unit:

(2)

where Y is O or S; R can be selected from H, alkyl (e.g., linear, branched, saturated, or unsaturated), aryl, heterocyclic, cycloaliphatic (e.g., saturated or unsaturated), or a metallocene (e.g., ferrocene, zirconocene or the like); n can be selected from 1 to 500; and a suitable base polymer such as a polyimide or epoxy resin.

In yet another aspect, embodiments of the present invention provide a method for boronating a polyphosphinohydrazide. In such embodiments, a phosphinohydrazide polymer of choice is reacted with trialkyl borane or a boronic acid. A phosphinohydrazide polymer can be obtained according to methods of synthesis disclosed in U.S. Pat. Nos. 4,403,075, 4,582,932, and 4,739,115, each of which is hereby incorporated by reference. Preferably, the reaction is carried out by adding the boronic acid to the neat polymer of choice and heating the mixture under agitation to a temperature between about 170° F. to 350° F., more preferably between about 250° F. to 350° F. Preferably, the phosphinohydrazide polymer has the following recurring structural unit:

(2)

where Y is O or S; R can be selected H, alkyl (e.g., linear, branched, saturated, or unsaturated), aryl, heterocyclic, cycloaliphatic (e.g., saturated or unsaturated), or a metallocene (e.g., ferrocene, zirconocene or the like); and n can be selected from 1 to 500.

Figure 1:
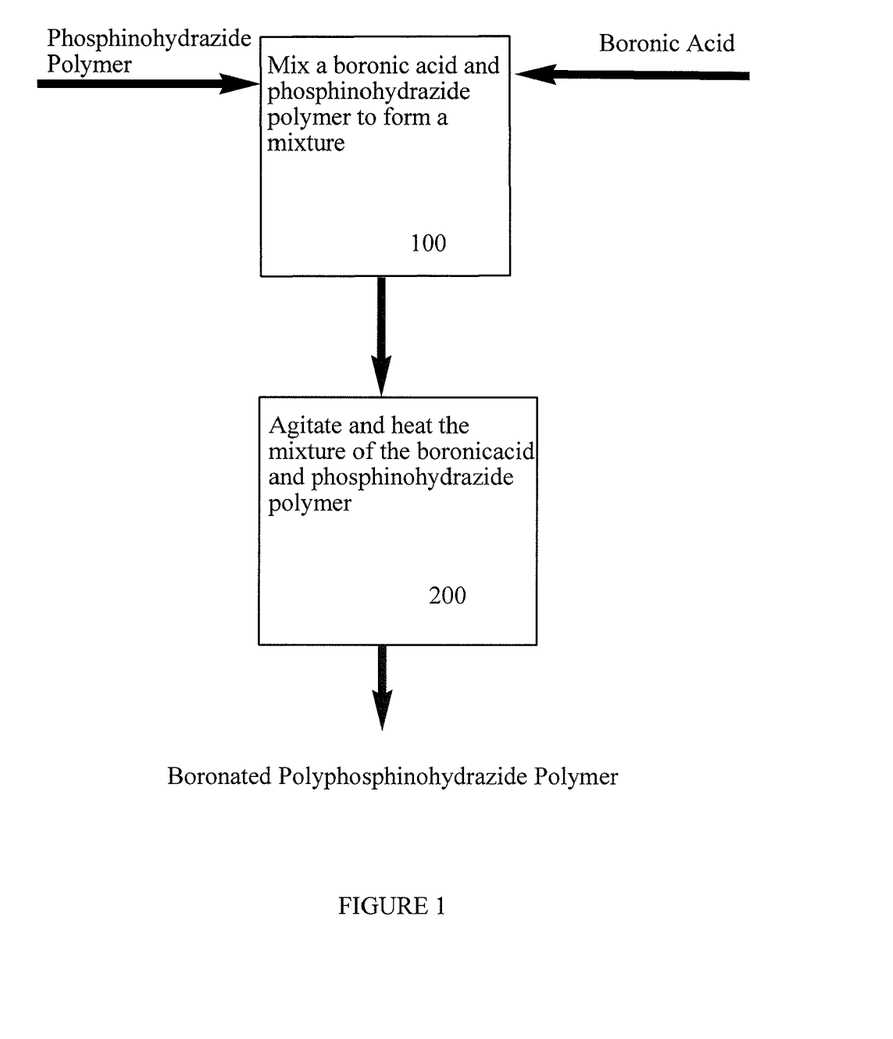
FIG. 1 is a flow chart illustrating a method for boronating a polyphosphinohydrazide according to embodiment of the present invention.

In the one embodiment according to the present invention illustrated in FIG. 1, a boronic acid and a phosphinohydrazide polymer are mixed 100 to form a mixture thereof. Preferably, the boronic acid is added to the neat phosphinohydrazide polymer. The resulting mixture from the mixing step 100 is then agitated and heated in a reaction step 200 to a temperature between about 170° F. to 350° F. to provide a boronated polyphosphinohydrazide polymer.

EXAMPLES

Bronated polyphosphinohydrazide polymers were prepared by heating varying percentages of boric acid with the corresponding phosphinohydrazide, viz., the P-methyl (i.e., R=methyl in Formula 1) and the P-hydrogen (i.e., R=hydrogen in Formula 1), to obtain the product used as a fire-retardant additive. However, the synthesis of the boronated product starts first with the synthesis of the polymethylphosphinohydrazide (hereinafter "P-M hydrazide") and the polyhydrophosphinohydrazide (hereinafter "P-H hydrazide").

Synthesis of Polyphosphinohydrazides

The first product prepared was polymethylphosphinohydrazide, where R=$CH_3$ in formula (1). Since this reaction does not become exothermic, it was prepared in bulk. Dimethyl methylphosphonate, in the amount of 248 g (2 moles), was placed in a 2-liter resin kettle. It was cooled in a dry ice-ethylene glycol bath and 100 g (2 moles) hydrazine hydrate were slowly added. The mixture was left to stir overnight and then heated to distill off the alcohol and water. The residue was a very viscous, light yellow product. The yield was 189 g (about 102%), the high yield being attributed to the confirmed formation of a methyl alcohol complex.

Polyphosphinohydrazide, where R=H in Formula (1), was prepared by reacting dimethylphosphite (DMP) with hydrazine hydrate, which resulted in the compound DMP/H. To minimize the exothermic nature of this reaction, it was carried out in the presence of xylene. Due to the fact that only the dimethylphosphite is soluble in xylene, in effect, this resulted in an interfacial polymerization. Dimethylphosphite, in the amount of 336.5 g (3.0 moles), was dissolved in 1 liter of xylene in a 2-liter resin kettle fitted with a stirrer, Claisen takeoff head, and a condenser. The mixture was cooled with a dry ice-ethylene glycol bath and 155 g (3.1 moles) of hydrazine hydrate were added slowly. The mixture was allowed to warm to room temperature and left to stir overnight. It was then heated to reflux at 140° F. for 48 hours, at which time alcohol and water were distilled off until the temperature rose to 284° F. It was refluxed at this temperature for two hours and then about 600 mls of xylene were distilled off. The remaining solution was transferred to a beaker, cooled, and the excess xylene was decanted off. The beaker was heated in a vacuum oven to remove the last trace of xylene. The yield of viscous, slightly yellow product was 328 g (representing about 140% of theoretical yield).

The presence of the methoxy groups was shown by both NMR analysis using a Perkin Elmer model nuclear magnetic resonance spectrometer and by infrared spectroscopy using Perkin Elmer Model 621 infrared spectrophotometer. Once again, methyl alcohol forms a stable complex with the phosphinohydrazide polymers.

Figure 2:
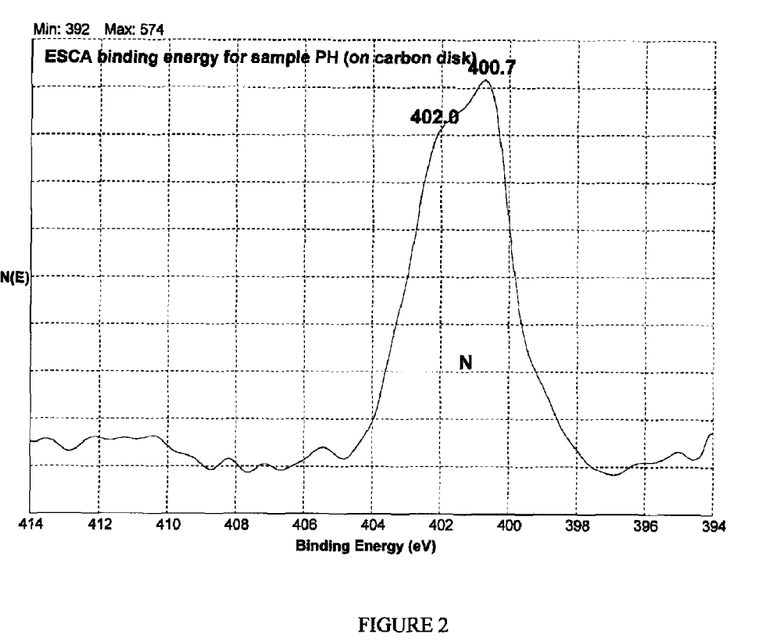
FIG. 2 illustrates the Electron Spectroscopy for Chemical Analysis (ESCA) spectra for a phosphinohydrazide polymer, which provides the binding energy of the polymer.

In addition to the infrared spectroscopic analysis, Electron Spectroscopy for Chemical Analysis (ESCA) and Auger analyses were done on the products obtained. As shown in FIG. 2, the ESCA binding energy spectra shows a doublet for nitrogen at around 400 and 402 ev. This implies that the nitrogen has two binding sites, each having a unique energy relationship with adjacent moieties. Thus, if we look at the structure represented by Formula (1), it is apparent that one bond of each nitrogen is to a phosphorous atom and the second is to a nitrogen atom. This aspect further ties in with the fire retarding capability in that, when exposed to a fire, nitrogen can readily split out as a gas and help blanket the flame, as well as having the phosphorous atom trap the oxygen radical (generated by a flame), thus reducing the burning tendency. Ultimately, the residue becomes a phosphorous carbide.

However, it was found that by introducing a boron atom into the polymers to form boronated polyphosphinohydrazide polymers according to Formula (2) increased or enhanced fire-resistance capability was achieved.

Synthesis of Boronated Polyphosphinohydrazides

The phosphinohydrazide polymers (R=H and R=$CH_3$ of Formula 1) were reacted with boric acid ($H_3BO_3$) in varying percentages. Boric acid was added to the neat P—H(R=H of Formula 1) and P—$CH_3$ (R=$CH_3$ of Formula 1) polymers and heated to about 190° F. with constant stirring. The boric acid slowly dissolved and was followed by vigorous gas evolution which subsided after about one hour. The gas was determined to be water/methanol (~60/40). No phosphates were found in the vapor. This evolution of methanol was further evidence that the phosphinohydrazide polymer had a methyl alcohol group attached (which was the reason for the high yield referenced earlier). As confirmed by the infrared spectra, the boric acid replaced the methanol.

The P—$CH_3$ (R=$CH_3$ of Formula 1) polymer formed clear solutions (when hot) with boric acid up to a 25% concentration but was hard and glassy at room temperature. Above 25% the solutions remained opaque and were firm and waxy at room temperature. The P—H polymer (R=H of Formula 1) formed clear solutions up to at least 50% boric acid (when hot) and were viscous, sticky liquids at room temperature up to 40% boric acid. Again, the infrared spectroscopic analysis and the ESCA and Auger analyses indicated the presence of the boron atom in the polymers.

The boronated polymers were tested for fire retardancy. About 20% of the boronated phosphinohydrazide polymer was added to a Monsanto 703 polyimide and used to impregnate a carbon cloth to make a composite laminate. The resultant panel was subjected to a 2500° F. flame test for 15 minutes. It did not burn and formed a stable char. The same test was performed with the phosphinohydrazide polymer without the boron, and it did not perform well at the 2500° F. flame temperature; although, it performed very well at 2000° F. The same test was run at 3000° F. and, again, the boronated polymer did well but the non-boronated sample did not.

Figure 3:
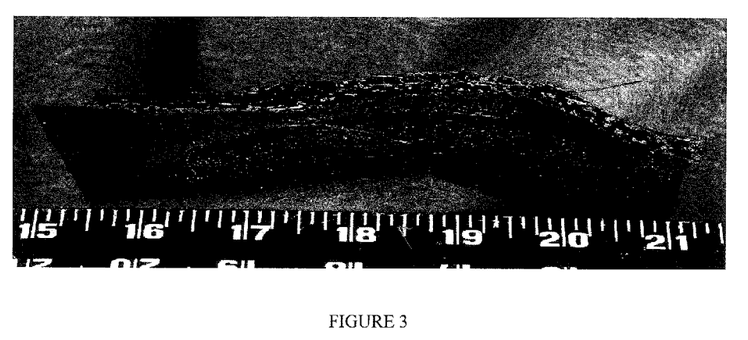
FIG. 3 is a first edge view of a brominated fire retardant panel after being flame-tested in a 2000° F. flame.
Figure 4:
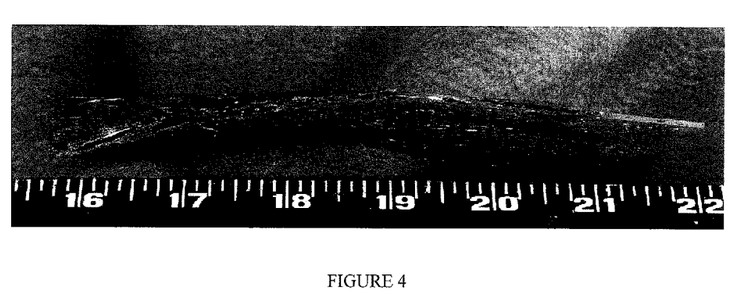
FIG. 4 is an opposite side edge view of the brominated fire retardant panel of FIG. 2.
Figure 5:
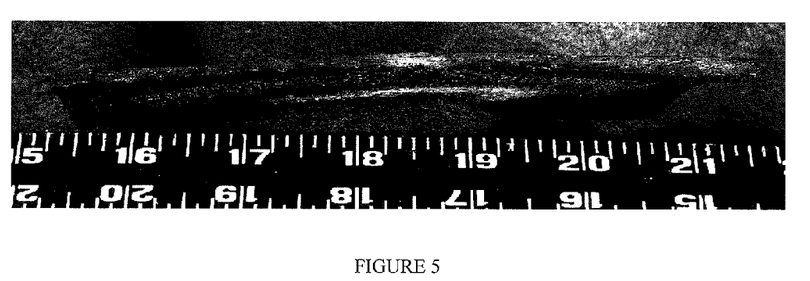
FIG. 5 is a first edge view of a boronated fire retardant panel, according to one embodiment of the present invention, after being flame-tested in a 2000° F. flame.
Figure 6:
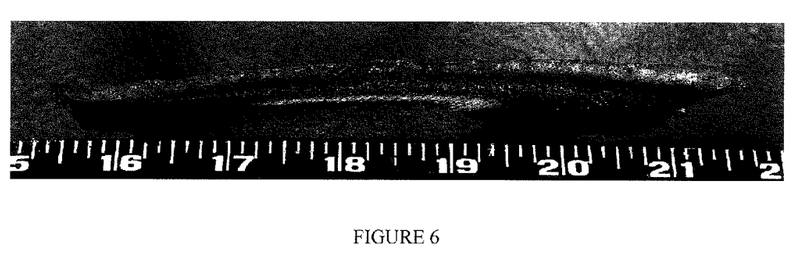
FIG. 6 is an opposite side edge view of the boronated fire retardant panel of FIG. 4.

Further work was done using the boronated phosphinohydrazide and an epoxy composite. The 20% boronated phosphinohydrazide polymer was added to an EA 9396 epoxy with a diaminodisulfone (DDS) hardener and impregnated into a 3K5HS carbon fabric. All panels prepared were four-ply and were vacuum bag cured for 30 minutes at 250° F. and post-cured for two hours at 350° F. When flame-tested in a 2000° F. flame, and compared to a brominated fire retardant (tetrabromobisphenol A), the brominated panel gave off a heavy, dark smoke and had a flame out on top of the panel after two minutes. However, the boronated panel had a flame out at one minute with a very light smoke. Furthermore, the plies of the brominated panel undesirably separated from each other (delaminated) as shown in FIGS. 3 and 4. FIG. 3 shows a first edge view of a brominated fire retardant panel after being flame-tested in a 2000° F. flame and FIG. 4 shows the opposite side edges of the same brominated fire retardant panel shown in FIG. 3. Additionally, the fabric on the flame side of the brominated fire retardant panel showed shreds of cloth. In contrast to the brominated fire retardant panel, the boronated fire retardant panel exhibited no delamination and formed a smooth, stable char on the flame side as illustrated in FIGS. 5 and 6. FIG. 5 shows a first edge view of a boronated fire retardant panel after being flame-tested in a 2000° F. flame and FIG. 6 shows the opposite side edges of the same boronated fire retardant panel shown in FIG. 5.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A boronated polyphosphinohydrazide having the basic structural unit:

wherein,
Y is O or S;
R is H, an unsaturated or saturated alkyl, an aryl, a heterocyclic, a cycloaliphatic, or a metallocene; and
n is from 1 to 500.

2. The boronated polyphosphinohydrazide according to claim 1, wherein R is H, a methyl, or a vinyl group.

3. The boronated polyphosphinohydrazide according to claim 1, wherein n is from 400 to 500.

4. A polymer resin, comprising a mixture of:
(A) a boronated polyphosphinohydrazide having the basic structural unit:

wherein,
Y is O or S;
R is H, an unsaturated or saturated alkyl, an aryl, a heterocyclic, a cycloaliphatic, or a metallocene;
n is from 1 to 500; and
(B) a base polymer selected from a polyimide, epoxy, acrylic, polyvinyl, phenolic/Novolak, polybenzimidazole, polyquinoxaline, polypyrrole, polyaniline, polyamide, polyaryl, polyamic acid, silicone resin or combinations thereof.

5. The polymer resin according to claim 4, wherein the base polymer is a polyimide or epoxy resin.

6. The polymer resin according to claim 4, wherein the boronated polyphosphinohydrazide comprises between 1 to 50% by weight of the polymer resin.

7. The polymer resin according to claim 4, wherein the boronated polyphosphinohydrazide comprises between 5 to 20% by weight of the polymer resin.

8. The polymer resin according to claim 4, wherein the mixture comprises:
(A) a boronated polyphosphinohydrazide selected from the group consisting of:

and wherein,
Y is O or S;
n is from 1 to 500; and
(B) a polyimide resin.

9. The polymer resin according to claim 4, wherein the mixture comprises:
(A) a boronated polyphosphinohydrazide selected from the group consisting of:

and wherein,

Y is O or S;
n is from 1 to 500; and
(B) an epoxy resin.

10. A fire resistant composite, comprising a cured mixture of:
(A) a boronated polyphosphinohydrazide having the basic structural unit:

wherein,
Y is O or S;
R is H, an alkyl, an aryl, a heterocyclic, and a cycloaliphatic;
n is from 1 to 500; and
(B) a base polymer selected from a polyimide, epoxy, acrylic, polyvinyl, phenolic/Novolak, polybenzimidazole, polyquinoxaline, polypyrrole, polyaniline, polyamide, polyaryl, polyamic acid, silicone resin or combinations thereof.

11. The fire resistant composite according to claim 10, wherein the base polymer is a polyimide or epoxy resin.

12. The fire resistant composite according to claim 10, wherein the boronated polyphosphinohydrazide comprises between 1 to 50% by weight of the polymer resin.

13. The fire resistant composite according to claim 10, wherein the boronated polyphosphinohydrazide comprises between 5 to 20% by weight of the polymer resin.

14. A method of making the boronated polyphosphinohydrazide of claim 1, comprising a step of reacting a phosphinohydrazide polymer and trialkyl borane or a boronic acid.

15. The method of claim 14, wherein the step of reacting a phosphinohydrazide polymer and trialkyl borane or a boronic acid comprises (i) mixing at least one phosphinohydrazide polymer and one of trialkyl borane or a boronic acid; (ii) agitating and heating the polymer and trialkyl borane or a boronic acid mixture to about 170° F. to 350° F.

16. The method of claim 14, wherein the phosphinohydrazide polymer has the following recurring structural unit:

wherein,
Y is O or S;
R is H, an alkyl, an aryl, a heterocyclic, a cycloaliphatic, or a metallocene; and
n is from 1 to 500.

* * * * *